US012806251B2

(12) United States Patent
Wu et al.

(10) Patent No.: US 12,806,251 B2
(45) Date of Patent: Nov. 24, 2026

(54) SEMAGLUTIDE SOLUBLE MICRONEEDLE COMPOSITION AND PREPARATION METHOD THEREFOR

(71) Applicant: GUANGZHOU NOVAKEN PHARM CO., LTD., Guangzhou (CN)

(72) Inventors: Chuanbin Wu, Guangzhou (CN); Beibei Yang, Guangzhou (CN)

(73) Assignee: Guangzhou Novaken Pharm Co., Ltd., Guangzhou (CN)

(*) Notice: Subject to any disclaimer, the term of this patent is extended or adjusted under 35 U.S.C. 154(b) by 274 days.

(21) Appl. No.: 18/722,038

(22) PCT Filed: Mar. 17, 2022

(86) PCT No.: PCT/CN2022/081495
§ 371 (c)(1),
(2) Date: Jun. 20, 2024

(87) PCT Pub. No.: WO2023/159702
PCT Pub. Date: Aug. 31, 2023

(65) Prior Publication Data

US 2025/0049892 A1 Feb. 13, 2025

(30) Foreign Application Priority Data

Feb. 22, 2022 (CN) ......................... 202210162729.3

(51) Int. Cl.
*A61K 38/26* (2006.01)
*A61K 9/00* (2006.01)
*A61K 38/47* (2006.01)
*A61K 47/10* (2017.01)
*A61K 47/32* (2006.01)

(52) U.S. Cl.
CPC ............ *A61K 38/26* (2013.01); *A61K 9/0021* (2013.01); *A61K 38/47* (2013.01); *A61K 47/10* (2013.01); *A61K 47/32* (2013.01); *C12Y 302/01035* (2013.01)

(58) Field of Classification Search
CPC ...................................................... A61K 38/26
See application file for complete search history.

(56) References Cited

U.S. PATENT DOCUMENTS

2008/0269666 A1 10/2008 Wang et al.

FOREIGN PATENT DOCUMENTS

| | | | |
|---|---|---|---|
| CA | 3096004 | A1 | 12/2019 |
| CN | 109153996 | A | 1/2019 |
| CN | 110022902 | A | 7/2019 |
| CN | 112274633 | A | 1/2021 |
| CN | 112741897 | A | 5/2021 |
| CN | 113347997 | A | 9/2021 |
| WO | 2020234384 | A1 | 11/2020 |
| WO | 2021089752 | A1 | 5/2021 |
| WO | 2021196546 | A1 | 10/2021 |

OTHER PUBLICATIONS

Hu et al., "Hyaluronidase-powered microneedles for significantly enhanced transdermal delivery efficiency", J. Controlled Release, 2023, vol. 353, pp. 380-390.*
International Search Report of PCT/CN 2022/081495, dated Nov. 30, 2022, 7 pages.
Written Opinion of the International Search Authority of PCT/CN 2022/081495, dated Nov. 30, 2022, 5 pages.
First Office Action of family patent CN 114470170 A, Jul. 28, 2023, 7 pages.
First Search for family patent CN 114470170 A, dated Jul. 26, 2023, 3 pages.

* cited by examiner

*Primary Examiner* — Suzanne M Noakes
(74) *Attorney, Agent, or Firm* — Hoffmann & Baron, LLP

(57) ABSTRACT

A semaglutide soluble microneedle composition and a preparation method therefor are disclosed. The soluble microneedle composition comprises a needle material and a base material. The needle material comprises semaglutide and hyaluronidase, and a mass ratio of semaglutide to hyaluronidase is (0.05-172):1. The semaglutide and the hyaluronidase are combined to prepare the soluble microneedle composition, so that the semaglutide can be better promoted to diffuse into the systemic circulation. Compared with a semaglutide oral tablet, the soluble microneedle composition has the advantages that the blood sugar regulating effect is improved by nearly 40 times, the bioavailability of semaglutide is improved, and the dosage and the cost of the hypoglycemic drug are reduced. Moreover, the soluble microneedle technology causes no pain during use and reduces the discomforts of users.

19 Claims, 2 Drawing Sheets

SEMAGLUTIDE SOLUBLE MICRONEEDLE COMPOSITION AND PREPARATION METHOD THEREFOR

CROSS-REFERENCE TO RELATED APPLICATIONS

The present application is a national phase entry under 35 USC § 371 of International Application PCT/CN2022/081495 filed Mar. 17, 2022, which claims the benefit of and priority to Chinese Patent Application No. 202210162729.3, filed Feb. 22, 2022, the entire disclosures of which are incorporated herein by reference.

TECHNICAL FIELD

The present disclosure relates to the technical field of biomedicine, and in particular to a semaglutide soluble microneedle composition and a preparation method therefor.

BACKGROUND

Glucagon-like peptide-1 (GLP-1) receptor agonists, as a new generation of hypoglycemic drugs, is second only to insulin in terms of hypoglycemic effect, and have multiple clinical advantages such as strong hypoglycemic effect, low risk of hypoglycemia, obvious weight loss effect and cardiovascular benefits. Diabetes is a progressive disease, while GLP-1 receptor agonists, as a transitional therapy between oral hypoglycemic drugs and insulin therapy, have the biological effect of delaying disease progression. According to the current trends of clinical applications, GLP-1 receptor agonists are one of the hypoglycemic drugs with the greatest market potential in the world.

Semaglutide, also known as Ozempic, is a glucagon-like peptide-1 (GLP-1) receptor agonist that stimulates insulin secretion in a glucose-dependent manner and reduces glucagon secretion, thereby lowering blood glucose. In the existing technology, semaglutide injection is usually administered by subcutaneous injection, which has a long-lasting effect. The semaglutide injection can be administered once a week, thereby better exerting the therapeutic effect. However, subcutaneous injection is an invasive administration method, and may cause problems such as pains and discomforts at the injection site, bringing physical and psychological discomforts to patients. Meanwhile, the injection pens used for drug administration cannot be reused, and the cost of the injection pens accounts for a large part of the cost of research and development, production and use of injections. In addition, there are problems such as complicated filling process for subcutaneous injection.

Semaglutide injection (trade name: Ozempic) has shown advantages in blood glucose reduction, weight loss and cardiovascular system, etc., after being approved for marketing in 2017. Novo Nordisk overcame the technical limitations of susceptibility of peptide drugs to degradation by digestive enzymes, and developed the oral preparation semaglutide tablets (trade name: Rybelsus), which were officially approved for marketing by the U.S. Food and Drug Administration (FDA) in September 2019 for the blood glucose control of adult patients with T2DM. Sodium N-(8-[2-hydroxylbenzoyl]amino) caprylate (SNAC) technology can prevent the destruction of semaglutide in the stomach and promotes cellular absorption through the gastric membrane, allowing semaglutide to reach systemic circulation. Although oral administration of semaglutide enhances compliance of patients, its bioavailability is only 0.9-1.2%, far less than that of subcutaneous injection. In addition, the oral semaglutide needs to be frequently administered once a day.

Soluble microneedles have the advantages of no pain, high efficiency and easy operation, etc., and can deliver drugs into the skin by breaking the stratum corneum barrier, making transdermal drug delivery possible. However, because the skin extracellular matrix is a complex macromolecular network, it plays an important role in regulating a variety of cellular mechanisms such as proliferation, adhesion, and migration. Hyaluronic acid is an important component of the skin's extracellular matrix, and its function in the tissue matrix is to limit the diffusion of water and other extracellular substances, including the diffusion of drugs. This causes most macromolecular drugs to remain on the superficial skin, unable to effectively diffuse into the skin and enter the systemic circulation, greatly reducing the bioavailability of drugs.

SUMMARY

In order to overcome the aforementioned problems in the existing technology, one of the objectives of the present disclosure is to provide a semaglutide soluble microneedle composition that combines semaglutide and hyaluronidase. Surprisingly, it is found that it can effectively solve the problem that the current semaglutide microneedle is difficult to penetrate into the blood and remains in the epidermal layer during use because of a large molecular weight of semaglutide. In addition, the soluble microneedle composition of the present disclosure is nearly 40 times more effective in regulating blood glucose than semaglutide oral tablets, which greatly improves the bioavailability of the soluble microneedle composition in the present disclosure.

A second objective of the present disclosure is to provide a method for preparing the semaglutide soluble microneedle composition.

In order to achieve the above objectives, the following technical solution is used in the present disclosure.

In a first aspect, the present disclosure provides a semaglutide soluble microneedle composition, including a needle material and a base material, where the needle material includes semaglutide and hyaluronidase in a mass ratio of semagluti (0.05-172):1.

Preferably, the mass ratio of semaglutide to hyaluronidase is (1-100):1; more preferably, the mass ratio of semaglutide to hyaluronidase is (1-50):1; still more preferably, the mass ratio of semaglutide to hyaluronidase is (1-30):1; and still more preferably, the mass ratio of semaglutide to hyaluronidase is (4-10):1.

Preferably, the needle material includes the following components in percentage by mass: 2.5%-51.5% of semaglutide, 0.3%-45.5% of hyaluronidase, 32%-96% of a polymer skeleton material, and 0.02%-0.8% of a pH regulator.

Preferably, the pH regulator includes at least one of sodium hydroxide, potassium hydroxide, or sodium carbonate. More preferably, the pH regulator is sodium hydroxide.

Preferably, a mass percentage of semaglutide is 5%-50%; more preferably, a mass percentage of semaglutide is 20%-45%; and still more preferably, a mass percentage of semaglutide is 35%-45%.

Preferably, a mass percentage of hyaluronidase is 1%-40%; more preferably, a mass percentage of hyaluronidase is 1%-25%; and still more preferably, a mass percentage of hyaluronidase is 5%-15%.

Preferably, a mass percentage of the polymer skeleton material is 40%-80%; more preferably, a mass percentage of the polymer skeleton material is 40%-60%; and still more preferably, a mass percentage of the polymer skeleton material is 45%-55%.

Preferably, a mass percentage of the pH regulator is 0.1%-0.8%; more preferably, a mass percentage of the pH regulator is 0.1%-0.5%; and still more preferably, a mass percentage of the pH regulator is 0.1%-0.3%.

Preferably, the polymer skeleton material includes at least one of polyvinylpyrrolidone/vinyl acetate copolymer, polyvinylpyrrolidone, or N-(2-hydroxypropyl) methacrylamide copolymer. More preferably, the polymer skeleton material is polyvinylpyrrolidone/vinyl acetate copolymer, i.e., PVP/VA. The PVP/VA is a linear copolymer of N-vinylpyrrolidone (NVP) and vinyl acetate (VA), which has the properties of PVP and PVAC, and retains satisfactory water solubility, adhesion and film-forming properties of PVP. In addition, as compared with PVP, the PVP/VA has relatively much lower water absorption, broader solubility, better plasticity and stronger surface activity, and is used as a microneedle skeleton material with excellent properties in the present disclosure.

Preferably, the polyvinylpyrrolidone/vinyl acetate copolymer includes at least one of PVP/VA 64, PVP/VA 64W, or PVP/VA 73W. More preferably, the polyvinylpyrrolidone/vinyl acetate copolymer is PVP/VA 64.

Preferably, the base material includes at least one of polyvinylpyrrolidone, polyvinyl alcohol, or sodium carboxymethyl cellulose.

Preferably, an alcohol liquid includes at least one of ethanol or propylene glycol.

Preferably, the polyvinylpyrrolidone includes at least one of PVP K90, PVP K30, or PVP K60. More preferably, the polyvinylpyrrolidone is PVP K90.

Preferably, a mass ratio of the needle material to the base material is (0.5-3.5):100; more preferably, a mass ratio of the needle material to the base material is (1-3):100; and still more preferably, a mass ratio of the needle material to the base material is (1-2):100.

In a second aspect, the present disclosure provides a method for preparing the semaglutide soluble microneedle composition provided in the first aspect of the present disclosure, including the following steps:

S1: preparing a needle material solution and a base material solution;
S2: adding the needle material solution to a microneedle female mold and centrifuging; and
S3: adding the base material solution to the microneedle female mold, centrifuging, then drying and demoulding, to obtain the semaglutide soluble microneedle composition.

Preferably, a step of preparing the base material solution includes: mixing an alcohol liquid with polyvinylpyrrolidone evenly. When the alcohol liquid is mixed with polyvinylpyrrolidone, swelling of polyvinylpyrrolidone occurs.

Preferably, in preparing the base material solution, the mixing is conducted for 6-24 h; more preferably, the mixing is conducted for 8-18 h; and still more preferably, the mixing is conducted for 8-15 h.

Preferably, in preparing the base material solution, the mixing includes at least one of stirring, ultrasound, or shaking. More preferably, in preparing the base material solution, the mixing is conducted by stirring.

Preferably, in preparing the base material solution, a speed of the stirring is 500-3,000 rpm; more preferably, a speed of the stirring is 1,000-3,000 rpm; and still more preferably, a speed of the stirring is 1,500-2,500 rpm.

Preferably, a step of centrifuging includes: conducting centrifugation at a speed of 3,800-4,500 rpm for 5-40 mins.

Preferably, the speed of centrifugation is 4,000-4,500 rpm. More preferably, the speed of centrifugation is 4,000-4,300 rpm.

Preferably, the centrifugation is conducted for 10-40 mins. More preferably, the centrifugation is conducted for 10-30 mins.

Preferably, steps for preparing the needle material solution include: mixing hyaluronidase with a solvent, then mixing with a polymer skeleton material to obtain an auxiliary material solution; and adjusting a pH of the auxiliary material solution, and then mixing the auxiliary material solution with semaglutide to obtain the needle material solution.

Preferably, a step of adjusting the pH of the auxiliary material solution includes: adjusting the pH of the auxiliary material solution to 6.5-7.5.

Preferably, in a step of drying, the drying is conducted at a temperature of 20-40 °C; more preferably, the drying is conducted at a temperature of 20-30 °C; and still more preferably, the drying is conducted at a temperature of 25-30 °C.

Preferably, in the step of drying, the drying is conducted for 20-50 h; more preferably, the drying is conducted for 25-40 h; and still more preferably, the drying is conducted for 30-40 h.

Preferably, the step of drying is conducted in a desiccator.

Preferably, a step of preparing the base material solution includes: mixing a base material with an alcohol liquid.

Preferably, a mass ratio of the alcohol liquid to the base material is (2-4.5):1; more preferably, a mass ratio of the alcohol liquid to the base material is (2.5-4.5):1; and still more preferably, a mass ratio of the alcohol liquid to the base material is (3-4.5):1.

The present disclosure can achieve the following beneficial effects.

In the present disclosure, semaglutide is combined with hyaluronidase to prepare a soluble microneedle composition, which can facilitate the diffusion of semaglutide into the systemic circulation. The soluble microneedle composition of the present disclosure is nearly 40 times more effective in regulating blood glucose than semaglutide oral tablets, which greatly improves the bioavailability of semaglutide, reduces the amount and cost of hypoglycemic drugs. In addition, the soluble microneedle technology causes no pain during use and reduces the discomforts of users.

Furthermore, the bioavailability of the soluble microneedle composition in the present disclosure is significantly higher than that of conventional microneedles which do not contain hyaluronidase, with a significant difference of $p<0.05$. Therefore, the problem that the conventional semaglutide microneedle is difficult to penetrate into the blood and remains in the epidermal layer because of a large molecular weight of semaglutide is solved.

DETAILED DESCRIPTION

Figure 1:
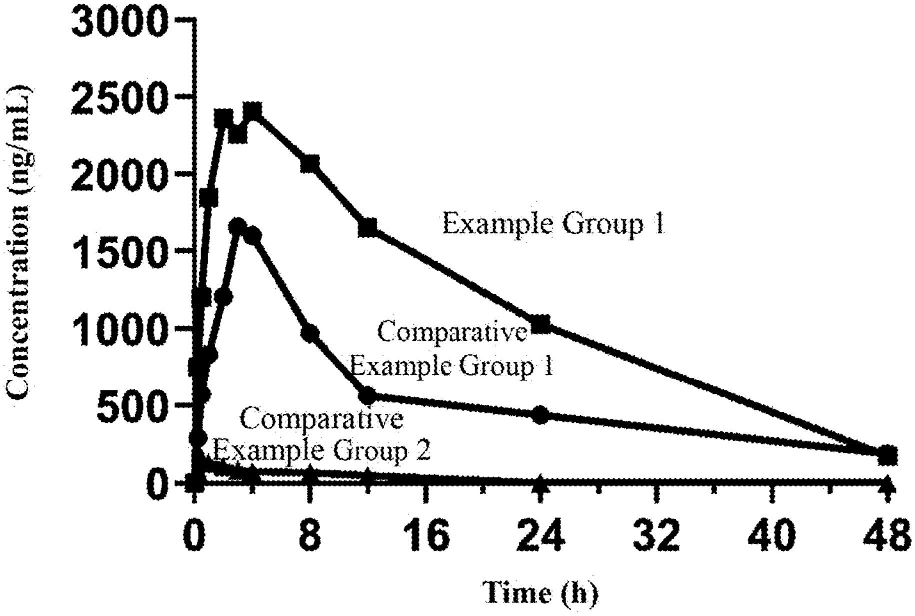
FIG. 1 is a diagram showing pharmacokinetic testing results of Example Group 1, Comparative Example Group 1 and Comparative Example Group 2.

The embodiments of the present disclosure will be further described in detail below with reference to the accompanying drawings and examples, but the embodiments and protection scope of the present disclosure are not limited thereto. It should be noted that any process that is not specifically described in detail below can be implemented or understood by those skilled in the art with reference to the existing technology. Reagents or instruments whose manufacturers are not indicated are conventional products that are commercially available.

Example 1

Components of the semaglutide soluble microneedle composition in this example were shown in Table 1 below.

TABLE 1

Components of the semaglutide soluble microneedle composition and proportions thereof

| Components | | Mass Percentages (%) |
|---|---|---|
| Needle material | Semaglutide | 39.23 |
| | Hyaluronidase | 7.13 |
| | PVP/VA 64 | 53.50 |
| | NaOH | 0.14 |
| Base material | PVP K90 | 100 |

The semaglutide soluble microneedle composition in this example was prepared by the following method.

1. Raw materials for preparing microneedles were weighed according to the raw materials and their proportions shown in Table 2 below.

TABLE 2

Raw materials of the semaglutide soluble microneedle composition and proportions thereof

| Raw Materials | | Mass Percentages (%) |
|---|---|---|
| Needle material solution | Semaglutide | 5.5 |
| | Hyaluronidase | 1 |
| | PVP/VA 64 | 7.5 |
| | NaOH | 0.02 |
| | Ultrapure water | 85.98 |
| Base material solution | PVP K90 | 25 |
| | Anhydrous ethanol | 75 |

2. Preparation of a needle material solution included the following steps:

1) adding hyaluronidase at a formula amount to a centrifuge tube, then adding ultrapure water at a formula amount for dissolving the hyaluronidase under stirring to obtain a hyaluronidase solution;

2) adding PVP/VA at a formula amount to the hyaluronidase solution, stirring to dissolve to obtain an auxiliary material solution;

3) adding dropwise a NaOH solution with a concentration of 0.25 mmol/L to the auxiliary material solution to adjust a pH of the auxiliary material solution to 7.0; and 4) accurately weighing semaglutide at a formula amount, adding to the above auxiliary material solution, and stirring to dissolve to obtain a needle material solution.

3. Preparation of a base material solution included the following steps:

weighing PVP K90 at a formula amount and then adding to a 50-mL centrifuge tube, adding anhydrous ethanol at a formula amount to the 50-mL centrifuge tube, stirring to swell overnight to obtain a base material solution.

4. Preparation of a soluble microneedle composition included the following steps:

1) Pipetting 200 μL of the above needle material solution into a microneedle female mold, and centrifuging at 4,000 rpm for 10 mins at 0-10 °C;

2) taking out the microneedle female mold, scraping off a remaining needle material solution on an upper layer for recycling, and continuing to centrifuge at 4,000 rpm for 30 mins at 0-10 °C;

3) adding the above base material solution to the microneedle female mold, and centrifuging at 4,000 rpm for 5 mins at 0-10 °C; and 4) drying the microneedle female mold in a desiccator for 36 h, carefully peeling off the microneedle female mold to obtain the semaglutide soluble microneedle composition in this example.

Example 2

Components of the semaglutide soluble microneedle composition in this example were shown in Table 3 below.

TABLE 3

Components of the semaglutide soluble microneedle composition and proportions thereof

| Components | | Mass Percentages (%) |
|---|---|---|
| Needle material | Semaglutide | 41.92 |
| | Hyaluronidase | 0.76 |
| | PVP/VA 64 | 57.17 |
| | NaOH | 0.15 |
| Base material | PVP K90 | 100 |

The raw materials for preparing the semaglutide soluble microneedle composition in this example and their proportions were shown in Table 4 below. The soluble microneedle composition of this example was prepared using the raw materials and their proportions shown in Table 4 with reference to the preparation method of the soluble microneedle composition in Example 1. The components of the soluble microneedle composition in this example were shown in Table 3.

TABLE 4

Raw materials of the semaglutide soluble microneedle composition and proportions thereof

| Raw Materials | | Mass Percentages (%) |
|---|---|---|
| Needle material solution | Semaglutide | 5.5 |
| | Hyaluronidase | 0.1 |
| | PVP/VA 64 | 7.5 |
| | NaOH | 0.02 |
| | Ultrapure water | 86.88 |
| Base material solution | PVP K90 | 25 |
| | Anhydrous ethanol | 75 |

Example 3

Components of the semaglutide soluble microneedle composition in this example were shown in Table 5 below.

TABLE 5

| Components of the semaglutide soluble microneedle composition and proportions thereof | | |
|---|---|---|
| Components | | Mass Percentages (%) |
| Needle material | Semaglutide | 30.52 |
| | Hyaluronidase | 27.75 |
| | PVP/VA 64 | 41.62 |
| | NaOH | 0.11 |
| Base material | PVP K90 | 100 |

The raw materials for preparing the semaglutide soluble microneedle composition in this example and their proportions were shown in Table 6 below. The semaglutide soluble microneedle composition of this example was prepared using the raw materials and their proportions shown in Table 6 with reference to the preparation method of the soluble microneedle composition in Example 1. The components of the semaglutide soluble microneedle composition in this example were shown in Table 5.

TABLE 6

| Raw materials of the semaglutide soluble microneedle composition and proportions thereof | | |
|---|---|---|
| Raw Materials | | Mass Percentages (%) |
| Needle material solution | Semaglutide | 5.5 |
| | Hyaluronidase | 5 |
| | PVP/VA 64 | 7.5 |
| | NaOH | 0.02 |
| | Ultrapure water | 81.98 |
| Base material solution | PVP K90 | 25 |
| | Anhydrous ethanol | 75 |

Comparative Example 1

Components of the soluble microneedle composition in this comparative example were shown in Table 7 below.

TABLE 7

| Components of the soluble microneedle composition and proportions thereof | | |
|---|---|---|
| Components | | Mass Percentages (%) |
| Needle material | Semaglutide | 42.24 |
| | PVP/VA 64 | 57.61 |
| | NaOH | 0.15 |
| Base material | PVP K90 | 100 |

The method for preparing the soluble microneedle composition in this comparative example included the following steps:

(1) weighing raw materials for preparing microneedles according to the raw materials and their proportions shown in Table 8 below.

TABLE 8

| Raw materials of the soluble microneedle composition and proportions thereof | | |
|---|---|---|
| Raw Materials | | Mass Percentages (%) |
| Needle material solution | Semaglutide | 5.5 |
| | PVP/VA 64 | 7.5 |
| | NaOH | 0.02 |
| | Ultrapure water | 86.98 |
| Base material solution | PVP K90 | 25 |
| | Anhydrous ethanol | 75 |

2. Preparation of a needle material solution included the following steps:

1) accurately weighing PVP/VA at a formula amount, adding ultrapure water at a formula amount for dissolving the PVP/VA under stirring to obtain an auxiliary material solution;

2) adding dropwise a NaOH solution with a concentration of 0.25 mmol/L to the auxiliary material solution to adjust a pH of the auxiliary material solution to 7.0;

3) accurately weighing semaglutide at a formula amount, adding to the above auxiliary material solution, and stirring to dissolve to obtain a needle material solution.

3. Preparation of a base material solution included the following steps:

weighing 10 g of PVP K90 and then adding to a 50-mL centrifuge tube, adding 30 mL of anhydrous ethanol the 50-mL centrifuge tube, and stirring to swell overnight to obtain a base material solution.

4. Preparation of a soluble microneedle composition included the following steps:

1) Pipetting 200 μL of the above needle material solution into a microneedle female mold, and centrifuging at 4,000 rpm for 10 mins at 0-10 °C;

2) turning the microneedle female mold over 180° after centrifugation, and then continuing to centrifuge at 4,000 rpm for 10 mins at 0-10 °C;

3) taking out the microneedle female mold, scraping off a remaining needle material solution on the upper layer for recycling;

4) adding 0.5 mL of the above base material solution to the microneedle female mold, and centrifuging at 4,000 rpm for 5 mins at 0-10 °C; and 5) drying the microneedle female mold in a desiccator for 36 h, and carefully peeling off the microneedle female mold to obtain the soluble microneedle composition in the Comparative Example 1.

Property Testing (1) Testing of Pharmacokinetic Properties

In accordance with ethical requirements, 9 male Sprague-Dawley rats weighed 180-200 g each were selected. After 3 days of quarantine, these rats were randomly divided into 3 groups, i.e. Example Group 1, Comparative Example Group 1 and Comparative Example Group 2, 3 rats in each group. In Example Group 1, the rats were administered transcutaneously with the soluble microneedle composition of Example 1 on the back; in Comparative Example Group 1, the rats were administered transcutaneously with the soluble microneedle composition of Comparative Example 1 on the back; in Comparative Example Group 2, the rats were administered intragastrically with semaglutide tablets (trade name: Rybelsus, Semaglutide, oral preparation, 3 mg/tablet).

The method of administration was as follows. Rats were depilated on the back in advance; microneedles were fixed on the probes of a tension gauge, then the microneedles were applied to the back of rats at a force of 100 N and a speed of 500 mm/min, maintaining for 5 mins. After administration, the microneedles were fixed on the back of rats for 2 h and then removed. In Comparative Example Group 2, semaglutide tablets were crushed in a mortar, then transferred to a beaker, then a quantity of water was added to prepare a suspension; then the rats were administered intragastrically with the suspension. The dose in each group was 214 ug per rat. At 0, 0.25, 0.5, 1, 2, 3, 4, 8, 12, 24, and 48 h after administration, 0.5 mL of blood was collected to a centrifuge tube coated with heparin sodium on an inner wall, centrifuged at 5000 rpm for 10 mins to separate the plasma, and then stored in a refrigerator at −20 °C The plasma concentrations of semaglutide were detected by LC/MS, and the results were recorded in Tables 9 and 10. A plasma concentration-time curve was drawn according to the results in Tables 9 and 10, and the pharmacokinetic parameters were calculated. The pharmacokinetic testing results of Example Group 1, Comparative Example Group 1 and Comparative Example Group 2 were shown in FIG. 1. The pharmacokinetic parameters of Example Group 1, Comparative Example Group 1 and Comparative Example Group 2 were shown in Table 11.

TABLE 9

Plasma concentrations of semaglutide at 0-2 h in Example Group 1, Comparative Example Group 1 and Comparative Example Group 2

| Group | Plasma Concentrations of Semaglutide (ng/ml) | | | | |
|---|---|---|---|---|---|
| | 0 h | 0.25 h | 0.5 h | 1 h | 2 h |
| Example | 0.00 | 398.10 | 696.35 | 1250.19 | 1848.74 |
| Group 1 | 0.00 | 894.26 | 1414.13 | 2112.05 | 2357.33 |
| | 0.00 | 957.98 | 1491.45 | 2183.06 | 2874.41 |
| Comparative | 0.00 | 205.13 | 531.25 | 706.61 | 1076.77 |
| Example | 0.00 | 368.19 | 524.16 | 796.20 | 1207.10 |
| Group 1 | 0.00 | 301.26 | 657.88 | 999.27 | 1332.44 |
| Comparative | 0.00 | 78.48 | 178.49 | 120.36 | 108.56 |
| Example | 0.00 | 86.49 | 155.36 | 133.26 | 99.48 |
| Group 2 | 0.00 | 80.46 | 144.36 | 132.62 | 115.69 |

TABLE 10

Plasma concentrations of semaglutide at 3-48 h in Example Group 1, Comparative Example Group 1 and Comparative Example Group 2

| Group | Plasma Concentrations of Semaglutide (ng/ml) | | | | | |
|---|---|---|---|---|---|---|
| | 3 h | 4 h | 8 h | 12 h | 24 h | 48 h |
| Example | 1810.67 | 2146.94 | 2000.94 | 1651.48 | 1001.03 | 159.57 |
| Group 1 | 2216.21 | 2476.56 | 1875.80 | 1574.57 | 945.62 | 159.07 |
| | 2754.04 | 2597.76 | 2326.51 | 1741.06 | 1139.97 | 199.14 |
| Comparative | 1514.91 | 1399.42 | 1059.02 | 684.39 | 333.08 | 180.41 |
| Example | 1645.47 | 1621.67 | 833.13 | 527.19 | 474.12 | 160.27 |
| Group 1 | 1819.01 | 1790.64 | 1016.32 | 476.63 | 507.29 | 221.87 |
| Comparative | 84.19 | 76.13 | 61.33 | 49.59 | 0.00 | 0.00 |
| Example | 79.49 | 72.16 | 71.24 | 50.74 | 0.00 | 0.00 |
| Group 2 | 89.13 | 70.26 | 65.14 | 47.16 | 0.00 | 0.00 |

TABLE 11

Pharmacokinetic Parameters

| Group | $T_{max}$(h) | $C_{max}$(ng/ml) | $AUC_{0-48h}$ (h*ng/mL) | Frel(%) |
|---|---|---|---|---|
| Example Group 1 | 4 | 2407 | 54770 | 43.89 |
| Comparative Example Group 1 | 3 | 1660 | 26305 | 21.08 |
| Comparative | 0.5 | 159.4 | 1208 | 0.97 |

TABLE 11-continued

Pharmacokinetic Parameters

| Group | $T_{max}$(h) | $C_{max}$(ng/ml) | $AUC_{0-48h}$ (h*ng/mL) | Frel(%) |
|---|---|---|---|---|
| Example Group 2 | | | | |

As shown in Tables 9 and 10, when the soluble microneedle composition of the present disclosure is administered at low doses, the plasma concentrations after administration are still high and are increased greatly compared with those administered with the soluble microneedle composition containing no hyaluronidase of Comparative Example 1, indicating that the rate of semaglutide in the Example 1 penetrating into the skin is significantly higher than that of the Comparative Example 1, and the soluble microneedle composition of Example 1 can achieve faster curative effect for regulating the blood glucose levels. In addition, the high plasma concentration after administration of the soluble microneedle composition of the present disclosure can maintain for a long time up to 24 h. This indicates that, the soluble microneedle composition of Example 1 can be administered at a longer interval when used for regulating the blood glucose levels, and the treatment dosage and cost are lower. As shown in Table 11 and FIG. 1, when semaglutide was combined with hyaluronidase, the soluble microneedle composition of the present disclosure has an increased bioavailability, and the introduction of hyaluronidase facilitates the penetration of semaglutide in the skin.

(2) Testing of Pharmacokinetic Properties of Microneedles with Different Concentrations of Hyaluronidase In accordance with ethical requirements, 6 male Sprague-Dawley rats weighed 180-200 g each were selected. After 3 days of quarantine, these rats were randomly divided into 2 groups, i.e. Example Group 2 and Example Group 3, 3 rats in each group. In Example Group 2, the rats were administered transcutaneously with the soluble microneedle composition of Example 2 on the back; in Example Group 3, the rats were administered transcutaneously with the soluble microneedle composition of Example 3 on the back.

Figure 2:
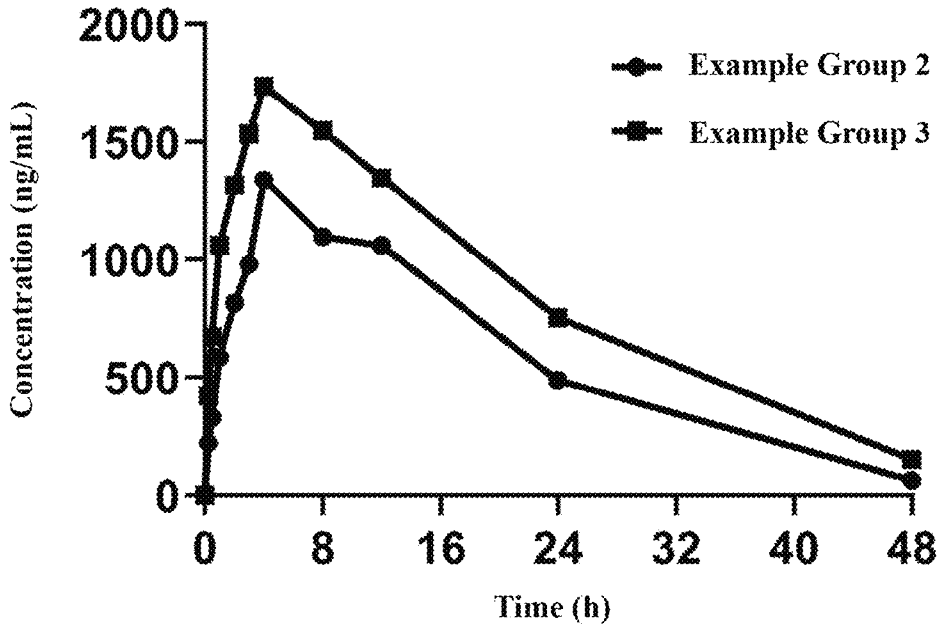
FIG. 2 is a diagram showing pharmacokinetic testing results of Example Group 2 and Example Group 3.

The method of administration was as follows. Rats were depilated on the back in advance; microneedles were fixed on the probes of a tension gauge, then the microneedles were applied to the back of rats at a force of 100 N and a speed of 500 mm/min, maintaining for 5 mins. After administration, the microneedles were fixed on the back of rats for 2 h and then removed. The administered dose in each group was 214 ug/rat. At 0, 0.25, 0.5, 1, 2, 3, 4, 8, 12, 24, and 48 h after administration, 0.5 mL of blood was collected to a centrifuge tube coated with heparin sodium on an inner wall, centrifuged at 5000 rpm for 10 mins to separate the plasma, and then stored in a refrigerator at −20 °C The plasma concentrations of semaglutide were detected by LC/MS, and the results were recorded in Tables 12 and 13. A plasma concentration-time curve was drawn according to the results in Tables 2 and 13, and the pharmacokinetic parameters were calculated. The pharmacokinetic testing results of Example Group 2 and Example Group 3 were shown in FIG. 2. The pharmacokinetic parameters of Example Group 2 and Example Group 3 were shown in Table 14.

TABLE 12

Plasma concentrations of semaglutide at 0-2 h in Example Group 2 and

| Group | Plasma Concentrations of Semaglutide (ng/ml) | | | | |
|---|---|---|---|---|---|
| | 0 h | 0.25 h | 0.5 h | 1 h | 2h |
| Example | 0.00 | 448.88 | 567.33 | 980.53 | 1389.14 |
| Group 2 | 0.00 | 92.52 | 191.44 | 440.77 | 568.77 |
| | 0.00 | 118.99 | 227.29 | 335.45 | 491.21 |
| Example | 0.00 | 485.26 | 698.79 | 1096.65 | 1346.25 |
| Group 3 | 0.00 | 506.42 | 832.16 | 1230.21 | 1589.47 |
| | 0.00 | 277.35 | 488.21 | 849.48 | 1009.45 |

TABLE 13

Plasma concentrations of semaglutide at 3-48 h in Example Group 2 and Example Group 3

| Group | Plasma Concentrations of Semaglutide (ng/ml) | | | | | |
|---|---|---|---|---|---|---|
| | 3 h | 4 h | 8 h | 12 h | 24 h | 48 h |
| Example | 1716.91 | 1755.48 | 1907.67 | 1882.27 | 822.58 | 111.8 |
| Group 2 | 683.78 | 1571.01 | 720.32 | 631.29 | 324.06 | 34.37 |
| | 534.32 | 688.27 | 661.33 | 663.52 | 316.78 | 41.09 |
| Example | 1566.76 | 1710.63 | 1599.23 | 1269.34 | 756.21 | 199.64 |
| Group 3 | 1795.15 | 1887.78 | 1649.26 | 1489.48 | 807.32 | 149.65 |
| | 1239.59 | 1599.64 | 1392.66 | 1279.66 | 694.77 | 103.79 |

TABLE 14

Pharmacokinetic Parameters

| Group | $T_{max}$(h) | $C_{max}$(ng/ml) | $AUC_{0-48h}$ (h*ng/mL) | Frel(%) |
|---|---|---|---|---|
| Example Group 2 | 4 | 1338 | 28145 | 22.55 |
| Example Group 3 | 4 | 1733 | 40652 | 32.58 |

As shown in Tables 9 to 14, the peak concentration and bioavailability of Example 2 (0.1% of hyaluronidase included in the raw materials) are similar to those of Comparative Example 1 (without hyaluronidase), and those of Example 2 were slightly higher than those of Comparative Example 1. Moreover, by comparing FIG. 1 and FIG. 2, the plasma concentration of Comparative Example Group 1 decreases to about 500 ng/mL after administration for 12 h, which is possibly caused by retention of semaglutide in the skin, and slow penetration and release due to a large molecular weight. The plasma concentration of Example Group 2 after administration quickly reaches a peak and quickly eliminates at a nearly constant rate, indicating that adding hyaluronidase to the formula can facilitate the penetration to a certain extent and reduce the intradermal retention of semaglutide. By comparing Example 3 (5% of hyaluronidase included in the raw materials) and Example 1 (1% of hyaluronidase included in the raw materials), the plasma concentration and bioavailability of Example 3 does not increase with the increased proportion of hyaluronidase, but are less than those of Example 1. The possible reason is that, when the proportion of hyaluronidase increases, the impact on the mechanical strength of the microneedle body increases, and the amount and depth of needle materials entering the skin are weakened. Although the formula of Example 3 contains a higher proportion of hyaluronidase, its penetration-enhancing effect is still stronger than that of Example 2, proving that the hyaluronidase has a satisfactory transdermal penetration-enhancing effect.

The embodiments of the present disclosure have been described in detail above, but present disclosure is not limited thereto. Various changes can be made by those having ordinary skills in the art within the knowledge scope without departing from the gist of the present disclosure. Furthermore, the embodiments of the present disclosure and the characteristics in the embodiments may be mutually combined if not in collision.

The invention claimed is:

1. A semaglutide soluble microneedle composition, comprising a needle material and a base material, wherein the needle material comprises semaglutide and hyaluronidase in a mass ratio of (0.05-172):1.

2. The semaglutide soluble microneedle composition of claim 1, wherein the needle material comprises the following components in percentage by mass: 2.5%-51.5% of semaglutide, 0.3%-45.5% of hyaluronidase, 32%-96% of a polymer skeleton material, and 0.02%-0.8% of a pH regulator.

3. The semaglutide soluble microneedle composition of claim 2, wherein the polymer skeleton material comprises at least one of polyvinylpyrrolidone/vinyl acetate copolymer, polyvinylpyrrolidone, or N-(2-hydroxypropyl) methacrylamide copolymer.

4. The semaglutide soluble microneedle composition of claim 1, wherein the base material comprises at least one of polyvinylpyrrolidone, polyvinyl alcohol, or sodium carboxymethyl cellulose.

5. The semaglutide soluble microneedle composition of claim 1, wherein a mass ratio of the needle material to the base material is (0.5-3.5):100.

6. The semaglutide soluble microneedle composition of claim 2, wherein the pH regulator includes at least one of sodium hydroxide, potassium hydroxide, or sodium carbonate.

7. The semaglutide soluble microneedle composition of claim 3, wherein the polyvinylpyrrolidone/vinyl acetate copolymer includes at least one of PVP/VA 64, PVP/VA 64W, or PVP/VA 73W.

8. The semaglutide soluble microneedle composition of claim 2, wherein a mass percentage of semaglutide is 5%-50%.

9. The semaglutide soluble microneedle composition of claim 2, wherein a mass percentage of hyaluronidase is 1%-40%.

10. The semaglutide soluble microneedle composition of claim 2, wherein a mass percentage of the polymer skeleton material is 40%-80%.

11. The semaglutide soluble microneedle composition of claim 2, wherein a mass percentage of the pH regulator is 0.1%-0.8%.

12. A method for preparing the semaglutide soluble microneedle composition of claim 1, comprising the following steps:

S1: preparing a needle material solution and a base material solution;

S2: adding the needle material solution to a microneedle female mold and centrifuging; and S3: adding the base material solution to the microneedle female mold, centrifuging, then drying and demoulding, to obtain the semaglutide soluble microneedle composition;

wherein steps of preparing the needle material solution further comprise: mixing hyaluronidase with a solvent, then mixing with a polymer skeleton material to obtain an auxiliary material solution; and adjusting a pH of the auxiliary material solution, and then mixing the auxiliary material solution with semaglutide to obtain the needle material solution.

13. The method for preparing the semaglutide soluble microneedle composition of claim 12, wherein the step of centrifuging comprises: conducting centrifugation for 5-40 mins at a speed of 3,800-4,500 rpm.

14. The method for preparing the semaglutide soluble microneedle composition of claim 12, wherein a step of adjusting the pH of the auxiliary material solution comprise: adjusting the pH of the auxiliary material solution to 6.5-7.5.

15. The method for preparing the semaglutide soluble microneedle composition of claim 12, wherein a step of preparing the base material solution comprises: mixing the base material with an alcohol liquid, and a mass ratio of the alcohol liquid to the base material is (2-4.5):1.

16. The method for preparing the semaglutide soluble microneedle composition of claim 15, wherein an alcohol liquid comprises at least one of ethanol or propylene glycol.

17. The method for preparing the semaglutide soluble microneedle composition of claim 12, wherein the drying is conducted at a temperature of 20-40 °C.

18. The method for preparing the semaglutide soluble microneedle composition of claim 12, wherein the drying is conducted for 20-50 h.

19. The method for preparing the semaglutide soluble microneedle composition of claim 12, wherein the drying is conducted in a desiccator.

* * * * *